United States Patent [19]
Principe et al.

[11] 3,951,855
[45] Apr. 20, 1976

[54] BREATH ALCOHOL TEST MEDIUM

[75] Inventors: Andrew H. Principe, Mundelein; Emmett P. Glynn, Lemont, both of Ill.

[73] Assignee: Cand-Aire Industries, Inc., Highland Park, Ill.

[22] Filed: July 9, 1973

[21] Appl. No.: 377,383

Related U.S. Application Data

[60] Continuation-in-part of Ser. No. 160,780, July 8, 1971, abandoned, which is a division of Ser. No. 802,880, Feb. 27, 1969, Pat. No. 3,618,393.

[52] U.S. Cl. ............................ 252/408; 23/230 B; 23/232 R; 23/254 R; 53/22 R; 73/19; 73/421.5 R; 252/305; 252/372
[51] Int. Cl.² .................. C09K 3/00; G01N 31/00; G01N 33/00; C01B 2/00
[58] Field of Search .................. 252/408, 372, 305; 23/230 B, 232 R, 254 R; 73/421.5 R, 19; 53/22 R

[56] References Cited
UNITED STATES PATENTS

| | | | |
|---|---|---|---|
| 2,214,264 | 9/1940 | White | 252/372 |
| 2,742,321 | 4/1956 | Mina et al. | 252/305 |
| 3,221,946 | 12/1965 | Riley | 222/309 |
| 3,330,773 | 7/1967 | De Hart, Jr. | 252/305 |
| 3,387,425 | 6/1968 | Flanner | 252/305 |
| 3,455,654 | 7/1969 | McConnaughey | 23/232 R |
| 3,618,393 | 11/1971 | Principe et al. | 73/421.5 |

*Primary Examiner*—Leland A. Sebastian
*Assistant Examiner*—T. S. Gron
*Attorney, Agent, or Firm*—Gary, Juettner, et al

[57] ABSTRACT

A standard breath alcohol test medium comprises a canister containing a charge of nitrogen and vaporized alcohol having a predetermined amount of alcohol per unit of volume therein, and means on the canister accommodating discharge of the nitrogen and alcohol mixture therefrom, preferably by pressure discharge or hypodermic extraction through a self-sealing septum in the wall of the canister. A method for filling the containers with a predetermined amount of alcohol vapor is also disclosed.

5 Claims, 3 Drawing Figures

U.S. Patent   April 20, 1976   3,951,855
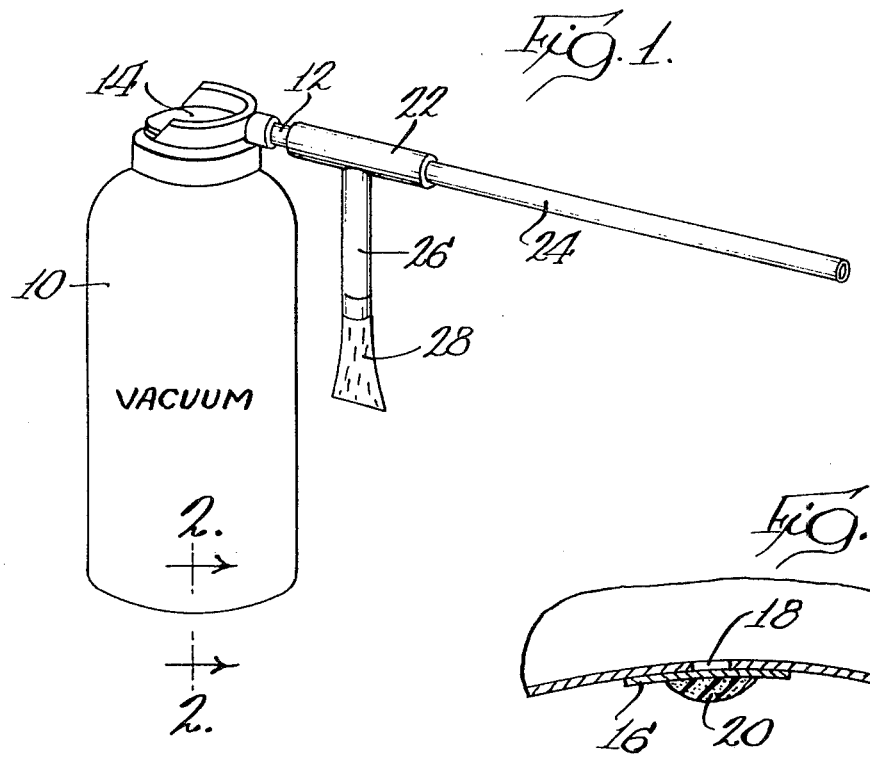
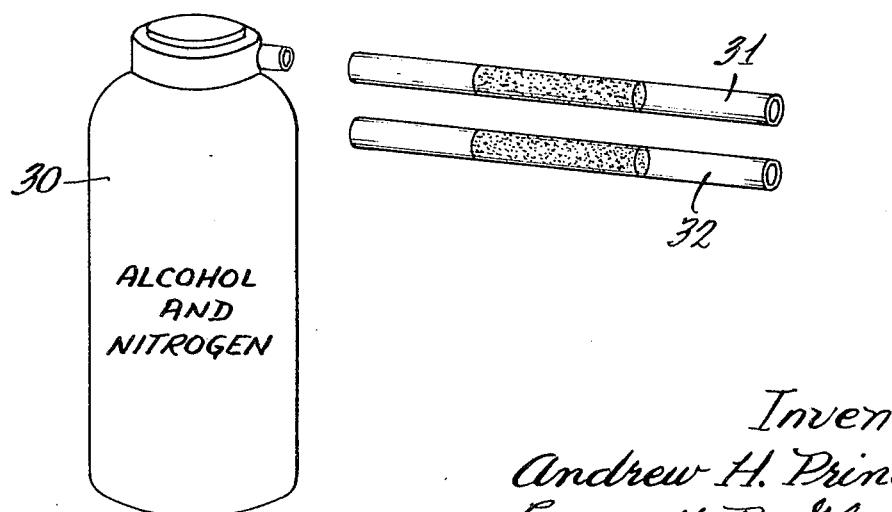
Inventors:
Andrew H. Principe
Emmett P. Glynn
By
Gary, Juettner, Pigott & Cullinan
Attys

BREATH ALCOHOL TEST MEDIUM

CROSS REFERENCE

This application is a continuation-in-part of our co-pending application, Ser. No. 160,780, filed July 8, 1971, now abandoned, which was a division of our application, Ser. No. 802,880, filed Feb. 27, 1969, which issued as U.S. Pat. No. 3,618,393.

BACKGROUND OF THE INVENTION

Many devices have heretofore been proposed for analysis of the breath, especially the deep lung or alveolar air, of persons suspected of drunk driving. Some of these devices have attained significant acceptance with the police and the courts, and are generally respected aids to traffic law enforcement. The amount of alcohol in the breath is proportional to the amount of alcohol in the blood; hence, breath testing provides reliable chemical evidence of the level of intoxication.

In accordance with our aforesaid parent application, we have discovered that a breath sample may be obtained in a reliable and convenient manner by the use of a partially evacuated valved canister having an inlet tube with a pressure relief valve. The suspect is required to blow into the tube for a period of time, and then the valve of the canister is opened, which draws a predetermined volume of the suspect's breath into the canister.

After the breath sample has been obtained, quantities of the sample may be withdrawn from the canister for testing. The amount of alcohol present in the sample may be determined by various methods, some of which involve comparison of the sample against a known quantity of alcohol.

Frequent calibration checks on the testing instrument are also necessary to render the results legally sufficient and to show that the instrument or other testing device was performing properly at the time the test was made. Any alcohol standard employed in connection with such tests must obviously be reliable and convenient to use without error on the part of the instrument operator. The possibility of a contaminated or unreliable alcohol standard will obviously undermine the validity of the test.

THE INVENTION

The present invention provides a method and apparatus for providing a standard sample of a known quantity of alcohol vapor per unit volume carried in an inert gaseous medium. A known amount of alcohol is injected into a closed, fixed volume container which contains a non-reactive gas, such as nitrogen either above or at atmospheric pressure. The amount of alcohol injected is sufficiently small to maintain complete vaporization of the sample in the container at ambient temperatures.

The container may be provided with a sealable port through which a predetermined volume of the alcohol and nitrogen mixture may be withdrawn, such as by syringe. If the sample is under pressure in the container, the sample may be emitted through a standard valve fitting. The volume of the mixture in the container will have a known quantity of vaporized alcohol which may be employed as a standard to calibrate or check an instrument or to perform a comparative test.

A particular advantage of the standard of the present invention is its portability, which allows on-the-spot comparisons of a suspect's breath to the standard. The standard may also be conveniently transported and incorporates features which render it foolproof and easy to use.

The vaporized alcohol sample is prepared by providing a pressurized gas space over liquid alcohol and bleeding the alcohol saturated gas off into evacuated or partially evacuated containers at a lower pressure, whereby the amount of alcohol in the gas is below the saturation level at a given pressure. This assures that the alcohol in the final container will be present entirely in vapor form.

The Drawing

FIG. 1 is a perspective view of the sample securing device as equipped for sampling the breath of a human being;

FIG. 2 is a fragmentary cross-sectional view of the bottom wall of the sample receiving canister, the view being taken substantially on line 2—2 of FIG. 1; and FIG. 3 is a perspective view of a canister having a standard quantity of alcohol therein and incorporating the principles of the present invention.

DESCRIPTION OF THE PREFERRED EMBODIMENT

Referring to FIGS. 1 and 2, the apparatus described and claimed in our said parent application comprises an evacuated canister 10 equipped with an inlet 12, a manually operated valve 14 for controlling said inlet to accommodate selective intake of gas into the canister, and a septum 16 in a wall of the canister accommodating hypodermic extraction of gas from the canister.

The canister may be any selected vessel or container conveniently and economically available, such as a glass, cardboard or metal container capable of being evacuated and of sufficient strength to withstand handling and shipment. In the preferred embodiment, a metal aerosol can is beneficially employed.

Aerosol cans conventionally comprise a metal body equipped at the upper end thereof with a tube communicating with the interior of the can and a finger operated valve for controlling communication between the interior of the can and atmosphere through said tube. The lower wall of the can is usually concave, and therefore provides an ideal, sheltered or protected space within which the septum 16 may be provided. For the purpose, the bottom wall of the can is centrally perforated to provide an access hole 18, which is then covered by a septum wall 16 of vinyl or the like adapted to be pierced by a hypodermic needle. To insure automatic self-sealing of the septum following piercing by a needle, the wall 16 is preferably covered by a globule 20 of self-sealing material, such as RTV-Silicone Rubber.

Further in accord with the invention, the interior of the can comprises or is coated with an inert material to prevent any reaction with or contamination of the gas sample to be taken. Also, a filter for screening out particulate matter is preferably embodied in the inlet 12. The can is preferably flushed with nitrogen or an inert gas prior to evacuating.

The can preferably has a volume or capacity to receive a gas sample of about 125 cc, which is several times the amount of gas required for gas chromatographic analysis, whereby the can receives sufficient gas to permit several separate analysis; and particularly to permit initial analysis plus retention of sufficient gas to accommodate reproduction of the analysis at a later date. However, any size canister may be used as desired or requied. To facilitate rapid taking of a sample, the can is preferably evacuated to about 25–26 inches of mercury, but again this is subject to variation as desired for particular circumstances.

To afford particular facility for the taking of human breath samples in drunkenness cases, each canister intended for this used is accompanied by a kit comprised of a T-tube 22 and a gas or breath tube 24, the T-tube including an exhaust leg or tube 26 having a very simple one-way valve 28 on its end. To prepare the sampler for use, one end of the tube 22 is pushed onto the inlet 12 of the can and the breath tube 24 is pushed into the other end of the tube 22.

The suspect breathes into the free end of the tube 24. The mouth and lung surface air are blown through the tubes 24 and 26 by the suspect, the same exhausting through the valve 28, which may simply be a limp tube of plastic normally collapsed on itself but adapted to be blown open by pressure from the tube 26, but to close tight upon reversal of the pressure balance. As the suspect reaches the end of a complete exhalation, the operator depresses the pushbuttom of valve 14 whereupon a sample of alveolar or deep lung air is quickly sucked into the interior of the canister. A highly reliable sample is thereby secured because the suspect has no control over the sample. Portions of the sample may then be withdrawn and analyzed for alcohol content.

In accordance with the present invention, a contained standard of a known amount of alcohol entirely in vaporized form is provided for use as a test medium. In general, the standard comprises a fixed volume container having a known amount of vaporized ethanol therein carried by a relatively unreactive gas, such as nitrogen or other inert gas. The amount of alcohol in the container is sufficiently small to insure that all alcohol is in vapor form at the pressure within the container and at ambient temperatures. The container is preferably pressurized with nitrogen to a predetermined pressure, which facilitates injection of the standard sample into a test instrument.

As shown in FIG. 3, the standard alcohol sample may be contained in a conventional aerosol canister 30 having a valved outlet to accommodate discharge of a pressurized sample. Containers having samples at atmospheric pressure may be provided with a septum in the bottom wall as shown in FIG. 2. Preferably, the interior of the container is coated with a material that is non-reactive with alcohol.

The standard may be prepared by evacuating the container, and then injecting a given amount of alcohol and inert gas into the container. Preferably, the container is flushed with nitrogen or other inert gas before evacuation to remove all traces of air.

In the preparation of the sample, care must be exercised to assure that all of the contained sample is in vapor form. Condensation of the vapor on the interior walls of the container would destroy the integrity of the sample. In order to assure good results, a large vessel having an inert atmosphere is partially filled with alcohol and is then pressurized with inert gas at room temperature, whereby an equilibrium of liquid-vapor is attained in the vessel, or the gas above the liquid alcohol becomes saturated with alcohol vapor. The pressure in the large vessel is not critical, but preferably is in the order of 350 pounds per square inch.

The saturated gas from the large vessel is then drained into an empty secondary container having an interior positive inert gas pressure which is lower than that in the large container, thereby assuring that all contained alcohol will remain in vapor form. The gas in the secondary container, for example, may be at a pressure of 10 to 25 lbs. per sq. in. The gas from the secondary container is then drained directly into metal canisters which have been evacuated or partly evacuated, from about 10 to 25 in. Hg being typical.

The canisters are then preferably pressurized with nitrogen or other inert gas. Again, the degree of final pressurization may vary with the intended use, but a pressure of 90 to 110 lbs. per sq. in. is generally preferred.

It may be seen that the aforesaid method of filling of the canister eliminates the possibility of alcohol condensation in the canister because of the large pressure reduction between the large vessel and secondary containers. The amount of alcohol vapor per unit volume may be easily determined from standard saturation tables. Moreover, the amount of alcohol within the canister may be varied by varying the degree of evacuation of the canister prior to filling, whereby different known amounts of alcohol may be introduced into respective containers.

Although the present invention is described in connection with standard alcohol vapor samples, it will be appreciated that other standard samples of relatively volatile liquids may be provided by the present method.

The standard sample of the present invention is most conveniently employed in connection with testing apparatus which measures a standard volume of gas before measuring alcohol content. For this purpose, a pressurized sample is employed and is connected directly to the apparatus. The samples may be used to test the accuracy of the analyzer or to test the operator of the instrument. The standard may be advantageously employed in connection with a wide variety of test instruments, including gas or liquid chromatographs and dichromate comparators.

To provide an instantaneous breath test, the apparatus of FIG. 3 may be employed, which comprises an aerosol can 30 like the canister 10 containing a standard breath alcohol sample and a pair of ampules 31 and 32 each containing a charge of chemicals that change color when exposed to or reacted with ethanol. These ampules may be used either (a) by having the suspect breathe into one and releasing a quantity of gas from the can 30 into the other and then comparing the colors of the ampules; or (b) by hypodermically withdrawing through the septums measured specimens from the sample can 10 and the standard can 30, injecting the measured specimens into the respective ampules and then comparing the colors of the two. For test (a) the can 30 would contain a pressurized charge of alcohol and nitrogen, and for test (b) the can 30 would be identical to can 10 and contain either a pressurized or nonpressurized charge of alcohol and nitrogen. Test (b) is more scientific and reliable.

In addition to the foregoing, the can 30 containing the standard breath alcohol medium may be used to test and calibrate simplified field versions of gas chromatographic apparatus and all spectrophotometric devices. In addition, cans 30 containing predetermined and variable quantities of alcohol can be used most advantageously to re-test the qualifications of personnel certified to conduct breath alcohol tests.

We claim:

1. A gaseous standard of a known amount of vaporized ethanol in a closed canister having interior walls which are inert to said ethanol comprising a charge of vaporized ethanol in a predetermined amount per volume of the canister, the remainder of the volume in said canister consisting essentially of a gaseous medium inert with respect to the vaporized ethanol contained therein, said charge of vaporized ethanol being present in said canister entirely in vapor form, and said canister having a means for accommodating discharge of said gaseous medium containing the known amount of ethanol vapor therefrom.

2. The standard of claim 1 wherein the gas pressure in said canister is above atmospheric pressure.

3. The standard of claim 2 wherein the gas pressure is in the order of about 10 to about 25 lbs. per sq. in.

4. A process for establishing a gaseous standard of a known amount of vaporized volatile liquid, comprising the steps of pressurizing a first container that is partially filled with said liquid with a gas which is inert to said liquid to a given pressure to produce a vaporized volatile liquid saturated gas, draining off the vaporized volatile liquid saturated gas into a secondary container at a pressure that is lower than the pressure of said first container, and then draining the vaporized volatile liquid containing gas from said secondary container into a dispensing container having a lower pressure than said secondary container.

5. The process of claim 4 comprising the additional step of pressurizing the smaller filled containers with gas to a pressure level below the pressure in the first container.

* * * * *